US009056140B2

(12) United States Patent
Stoloff et al.

(10) Patent No.: US 9,056,140 B2
(45) Date of Patent: Jun. 16, 2015

(54) PHARMACEUTICAL COMPOUND (75) Inventors: Gregory Alan Stoloff, London (GB); Wilson Romero Caparros-Wanderley, Aylesbury (GB)

(73) Assignee: Biocopea, Ltd. (GB)

( * ) Notice: Subject to any disclaimer, the term of this patent is extended or adjusted under 35 U.S.C. 154(b) by 980 days.

(21) Appl. No.: 12/677,701

(22) PCT Filed: Sep. 11, 2008

(86) PCT No.: PCT/EP2008/062071
§ 371 (c)(1),
(2), (4) Date: May 21, 2010

(87) PCT Pub. No.: WO2009/034136
PCT Pub. Date: Mar. 19, 2009

(65) Prior Publication Data
US 2010/0286062 A1 Nov. 11, 2010

(30) Foreign Application Priority Data

Sep. 14, 2007 (GB) .................................. 0718045.8

(51) Int. Cl.
*A61K 38/16* (2006.01)
*A61P 35/00* (2006.01)
*C07K 14/00* (2006.01)
*A61K 47/48* (2006.01)

(52) U.S. Cl.
CPC ..... *A61K 47/48061* (2013.01); *A61K 47/48261* (2013.01)

(58) Field of Classification Search
None
See application file for complete search history.

(56) References Cited

U.S. PATENT DOCUMENTS

| 5,478,804 | A | 12/1995 | Calabresi et al. | |
|---|---|---|---|---|
| 6,669,938 | B1 | 12/2003 | Rosenblum | |
| 7,153,977 | B2 * | 12/2006 | Lee ................. | 548/504 |
| 2004/0013691 | A1 | 1/2004 | Rosenblum | |
| 2004/0166167 | A1 * | 8/2004 | Li et al. ........... | 424/490 |

FOREIGN PATENT DOCUMENTS

| WO | 94/21813 A1 | 9/1994 |
|---|---|---|
| WO | 96/08274 A2 | 3/1996 |
| WO | 2005/121341 A1 | 12/2005 |
| WO | 2006/083961 A2 | 8/2006 |

OTHER PUBLICATIONS

Grese, PNAS, 94 1997.*
Press, Oncogene, 5, 7, 1990.*
Qi et al., "Binding and Cytotoxicity of Conjugated and Recombinant Fusion Proteins Targeted to the Gonadotropn-Releasing Hormone Receptor," Cancer Research, 2004, pp. 2090-2095, vol. 64.
Rosenblum et al., "A gelonin-containing immunotoxin directed against human breast carcinoma," Mol. Biotherapeutics, 1992, pp. 122-129, vol. 4.
Rosenblum et al., "Recombinant Immunotoxins Directed against the c-erb-2/HER2/neu Oncogene Product: In Vitro Cytotoxicity, Pharmacokinetics, and In Vivo Efficacy studies in Xenograft Models," Clinical Cancer Research,1999, pp. 865-874, vol. 5.
Tecce et al., "Characterization of Cytotoxic Activity of Saporin Anti-GP185/HER-2 Immunotoxins," Int. J. Cancer, 1993, pp. 122-127, vol. 55.
Chandler et al., "Targeting Tumor Cells via EGF Receptors: Selective Toxicity of an HBEGF-Toin Fusion Protein," Int. J. Cancer, 1998, pp. 106-111, vol. 78.
Krolick et al., "Specific Killing of a Human Breast Carcinoma Cell Line by a Monoclonal Antibody Coupled to the A-Chain of Ricin," Cancer Immunol. Immunother., 1981, pp. 39-41, vol. 12.
Vogel et al., "Effects of tomoxifen vs. raloxifene on the risk of developing invasive breast cancer and other disease outcomes: The NSABP Study of Tomoxifen and Raloxifene (STAR) P-2 trial," JAMA, 2006, pp. 2727-2741, vol. 295, No. 23.
Swaby et al., "SERMs for the treatment and prevention of breast cancer," Rev. Endocr. Metab. Diisorder, 2007, pp. 229-239, vol. 8.
Yang et al., "Cytotoxic Activity of Gonadotropin-Releasing Hormone (GnRH)-Pokeweed Antiviral Protein Conjugates in Cell Lines Expressing GnRH Receptors," Endocrinology, 2003, pp. 1456-1463, vol. 144, No. 4.
Yip et al., "Targeted Delivery and Enhanced Cytotoxicity of Cetuximab-Saporin by Photochemical Internalization in EGFR-Positive Cancer Cells," Molecular Pharm., 2007, pp. 241-251, vol. 4, No. 2.
Monami, Amelie, "International Search Report," PCT/EP2008/062071, Jul. 15, 2009.
Mountjoy, Philip, "Search Report Under Section 17(5)," Application No. GB0718045.8, Jan. 15, 2008.
Official Action, Russian Application No. 2010114755/15(020813), Jun. 6, 2011.
Swamy et al., "An Estradiol-Porphyrin Conjugate Selectively Localizes Into Estrogen Receptor-Positive Breast Cancer Cells," Bioorganic & Medicinal Chemsitry, 2002, pp. 3237-3243, vol. 10.
Vogel et al., "Effect of Tamoxifen vs. Raloxifene on the Risk of Developing Invasive Breast Cancer and Other Disease Outcomes," JAMA, Jun. 2006, pp. 2727-2741, vol. 295, No. 23.
Pasqualucci et al., Immunotoxin Therapy of Hematological Malignancies. Haematologica (1995); 80: 546-556.
Shang et al., "Molecular Determinants for the Tissue Specificity of SERMs." Science, 2002, 295 (5564), pp. 2465-2468.
Gacio et al., "Photodynamic Cell-Kill Analysis of Breast Tumor Cells with a Tamoxifen-Pyropheophorbide Conjugate." Journal of Cellular Biochemistry 2006, 99 (3) pp. 665-670.

\* cited by examiner

*Primary Examiner* — Susan Tran
*Assistant Examiner* — William Craigo
(74) *Attorney, Agent, or Firm* — One3 IP Management, P.C.; Dean G. Stathakis; Peter D. Weinstein (57) ABSTRACT

Provided is a compound comprising:
(a) a first component capable of binding to ER+ cell receptors; and
(b) a second component;
wherein the second component is a ribosome inactivating toxin and is conjugated to the first component.

18 Claims, 5 Drawing Sheets

PHARMACEUTICAL COMPOUND

CROSS REFERENCE TO RELATED APPLICATIONS

This application is a U.S. National Stage Application filed under 35 U.S.C. §371 and claims priority to International Application No. PCT/EP08/62071, filed Sep. 11, 2008, which application claims priority to Great Britain Application No. 0718045.8, filed Sep. 14, 2007, the disclosures of which are incorporated herein by reference in their entirety.

FIELD OF INVENTION

The present invention relates to the treatment of cancer comprising estrogen receptor positive (ER+) cancer cells and in particular the treatment of breast cancer. The inventors have provided a conjugate comprising a pharmaceutical component and a toxin component. The conjugate has superior ability to target and destroy ER+ cancer cells.

BACKGROUND OF THE INVENTION

Among women worldwide breast cancer is the most common cancer and the most common cause of death by cancer. Breast cancer is believed to be caused by a variety of factors, one of these factors being increased blood levels of estrogen. Much research has taken place in the field of estrogen receptor families and the differences between estrogen receptor cancer cells and normal estrogen receptor cells. The aim of such research has been to discover drugs which can treat breast cancer by suppressing production of estrogen in the body.

One such type of cancer comprises cells bearing estrogen receptor (ER+ cells). These are cells with a large number of estrogen receptors, typically around 200000 to 5 million. A normal non-cancerous estrogen receptor cell will have typically around 20000 to 80000 estrogen receptors. Cancer cells have an increased rate of division in the presence of estrogen, responding to even small quantities of the hormone, due to the large number of estrogen receptors.

Novel systemic therapies for breast cancer are discussed in *Surgical Oncology* 12 (2003) 277-287 (Soo Lo, Stephen R. D. Johnston). These include endocrine therapies such as pure anti-estrogens and selective estrogen receptor modulators (SERMs), monoclonal antibodies targeted against growth factor receptors, small molecule signal transduction inhibitors, vaccines and immunotherapy strategies, and anti-angiogenesis therapies.

One drug that has been shown to be effective in treatment of estrogen receptor positive cancer is tamoxifen. Tamoxifen is an example of a selective estrogen receptor modulator (SERM) acting as an antagonist to estrogen receptor positive cancerous cells by binding to the estrogen receptors on the cell surface and preventing binding of estrogen to the cells and thus inhibiting cell division. Even though it is an antagonist in breast tissue it acts as partial agonist on the endometrium and has been linked to endometrial cancer in some women. Therefore, endometrial changes, including cancer, are among tamoxifen's side effects.

It has also been suggested that a conjugate of tamoxifen and a porphyrin might be effective in the photodynamic treatment of cancer cells, whereby the porphyrin displays phototoxic activity on exposure to red light and has a stronger cell killing in MCF-7 breast cancer cells compared with an unconjugated porphyrin. Estradiol-porphyrin conjugates which selectively localise into estrogen receptor positive breast cancer cells for photodynamic therapy of breast cancer are also described in *Bioinorganic & medicinal Chemistry* 10 (2002) 3237-3243 (Swamy, James, Mohr, Hanson and Ray).

Other conjugates that have been researched for their effectiveness in treating cancer include antibody toxin conjugates. *British Journal of Haemotology* 2000, 110, 351-361 (Bolognesi, Polito et al.) discloses linking of ribosome inactivating proteins such as saporin to monoclonal antibodies for the treatment of Hodgkin's lymphoma. However, to date there has been no such product that has succeeded through the human trials into a licensed product.

Whilst the current drugs and therapies for treatment of cancer and in particular breast cancer on the market do slow down the division of these cancer cells, after a few years the cells mutate such that they are no longer effected by the drug and the drug becomes useless, with patients not responding to the treatment.

It is an aim therefore of the present invention to provide a new treatment for ER+ cancers, including in particular such breast cancers, which solves the above mentioned problems by destroying ER+ cancer cells rather than just reducing the rate of cell division of these cancer cells like the other SERM's and treatments do.

The above mentioned problems have been solved by the aspects and embodiments of the present invention outlined below.

SUMMARY OF THE INVENTION

Accordingly, the present invention provides a compound comprising:
(a) a first component capable of binding to ER+ cell receptors; and
(b) a second component;
wherein the second component is a ribosome inactivating toxin and is conjugated to the first component.

The first component is capable of binding to cells comprising estrogen receptors—so-called ER+ cells, or in other words capable of binding to ER+ cell receptors, or estrogen cell receptors. As has been mentioned above, in the present context, ER+ cell receptors are estrogen receptor positive cell receptors (ER+). These may be present on many cell types, and the present invention extends to components capable of binding to all ER+ receptors, irrespective of the cell type. However, typically cells of interest in the present invention are cancerous cells, which generally have a large number of estrogen receptors, typically around 200,000 to 5 million. All types of breast cancer cells are of particular interest in the present invention. In contrast, normal non-cancerous estrogen receptor cells will have typically around 20,000 to 80,000 estrogen receptors.

The specific identity of the first component is not especially limited, provided that it conforms to the above criteria. However, in a preferred embodiment the first component is a selective estrogen receptor modulator (SERM), such as a raloxifene compound.

Typically in the present invention, the ribosome inactivating toxin is a protein (a ribosome inhibiting protein toxin is termed an RIP toxin) and preferably the RIP is a type I RIP. Typically, such proteins operate by irreversibly blocking protein synthesis and causing cell death. The specific identity of the toxin is not especially limited, provided that it conforms to the above criteria. In a preferred embodiment the toxin is saporin.

In a preferred embodiment the compound has a stoichiometric ratio of the first component to the second component in the range from 0.5:1 up to N:1 where N is the total number of binding sites for the first component in the second component. The binding sites are not especially limited, except in that they should be capable of binding the first component to the second component. Typically, but not exclusively, the binding site is a tyrosine, or a lysine. In saporin there are up to 14 tyrosine binding sites and up to 23 lysine binding sites, each independently capable of serving as a binding site for a first component (i.e. N=14, N=23 or N=37, depending on whether only tyrosine, only lysine, or both tyrosine and lysine attachment points are utilised). Thus, preferred ranges are from 0.5:1 up to 37:1, preferably from 0.5:1 up to 23:1, more preferably from 0.5:1 up to 14:1. However, depending on which attachment points are utilised, any ratios within these ranges may be employed.

In further particularly preferred embodiments, the stoichiometric ratio of the first component to the second component is in the range from 0.5:1 to 8:1 (preferably 0.5:1 to less than 8:1), and more preferably from 0.5:1 to 2.5:1. Stoichiometries of from 0.5:1 to 7:1, 0.5:1 to 6:1, 0.5:1 to 5:1, 0.5:1 to 4:1, 0.5:1 to 3:1 and 0.5:1 to 2:1 are also preferred.

In this respect the stoichiometric ratio may refer to both the average stoichiometry and the molecular stoichiometry. For example a mixture comprising a conjugate with a 1:1 molecular stoichiometric ratio (i.e. one molecule of the first component conjugated to each molecule of the second component) and a conjugate with a 3:1 molecular stoichiometry (i.e. three molecules of the first component conjugated to each molecule of the second component) both in equal proportions will have an average stoichiometry of 2:1. In this manner non-integer stoichiometries are possible.

The present invention further provides a pharmaceutical composition comprising any of the compounds as described above.

In another aspect, the invention provides use of any of the compounds and compositions as described above in medicine.

A further aspect of the present invention provides the use of any of the above mentioned compounds or compositions for the manufacture of a medicament for the treatment of a cancer comprising ER+ cells. The type of ER+ cell cancer is not especially limited, but it is particularly preferred that the cancer is a breast cancer. The medicament is suitable for treating any mammals, and in particular human subjects are preferred. The method of administration is not particularly limited, but it is preferred that the medicament is suitable for injection or infusion (intravenous or otherwise) or oral administration in a subject.

The dosage employed in the medicament is not especially limited, provided that sufficient dose is provided to satisfy efficacy and toxicity requirements. In a preferred embodiment of the present invention the medicament is suitable for injection into the subject to achieve peak blood concentrations of the conjugate equivalent to 1% to 500% of the clinical peak blood concentration of the first component when used in an unconjugated form.

In a further preferred embodiment of the present invention the medicament is suitable for injection into the subject to achieve 80% to 140% of the clinical peak blood concentration of the first component when used in an unconjugated form.

In this respect the targeted blood concentrations of raloxifene are based on the human standard therapeutic peak concentration of raloxifene in blood (i.e. 0.5 ng/ml).

The present invention further provides a method of manufacturing any of the compounds as described above by reacting the first component with the second component to conjugate the first component with the second component.

The present invention further provides a method of treatment of cancer comprising ER+ cells and in particular breast cancer, which method comprises administering a medicament to a subject, wherein the medicament comprises any compound or composition as defined above.

The present inventors have surprisingly found that the conjugate compounds and compositions in accordance with the present invention provide an effective treatment of ER+ cancer cells whose use resulted in a significant initial reduction in the daily tumor volume as well as in an increased and sustained reduction in the rate of tumor growth while not significantly effecting the non cancerous ER+ cells.

DETAILED DESCRIPTION OF THE INVENTION

The present invention provides a compound comprising a first component capable of binding to ER+ cell receptors and a second component wherein the second component is typically a RIP Type I class toxin and is conjugated to the first component.

The first component for the present invention is capable of binding to ER+ cell receptors and provided that this functionality is maintained, the first component is not especially limited. However, as mentioned above, it has been found that any selective estrogen receptor modulator (SERM) compound is especially useful. The type of SERM is not especially limited but may include any of: fulvestrant, tamoxifen, raloxifene, toremifene, droloxifene, idoxifene and lasofoxifene. In particular, a raloxifene compound is particularly useful.

The second components is a ribosome inactivating toxin. As has been explained, it is preferably a protein (an RIP toxin) and further preferably a type I RIP. It is particularly preferred that the toxin cannot enter cells by itself and acts on internal workings of cells only.

Raloxifene, is a 510 Da selective estrogen receptor modulator (SERM) used in the prevention of osteoporosis in postmenopausal women. A recent clinical trial (Vogel V G; Costantino J P; et. al.; *for the National Surgical Adjuvant Breast and Bowel Project (NSABP). Effects of Tamoxifen vs Raloxifene on the Risk of Developing Invasive Breast Cancer and Other Disease Outcomes: The NSABP Study of Tamoxifen and Raloxifene (STAR) P-2 Trial. JAMA.* 2006; 295:2727-2741) has showed that raloxifene is as effective as tamoxifen in reducing the incidence of estrogen receptor positive breast cancer. However patients taking raloxifene daily had 36 percent fewer uterine cancers and 29 percent fewer blood clots than women taking tamoxifen daily. Uterine cancers, especially endometrial cancers, are a serious side effect of tamoxifen.

A raloxifene compound may take the following structure:

In the above structure any one or more of the hydrogens attached to carbons may be replaced by substituents.

The substituents for raloxifene are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, WA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination of two or more of the substituents and/or functional groups defined above.

When the second component for the present invention is an RIP Type I class toxin, it is not especially limited. It may be any of saporin, MOM, PAP-S, bouganin and gelanin and of these in particular saporin is useful as the toxin as part of the compound and pharmaceutical composition of the present invention.

Saporin is a 30 kDa Type I ribosome-inactivating protein (RIP) obtained from the seeds of the Soapwort plant (*Saponaria officinalis*). Saporin's N-glycosidase activity depurinates a specific nucleotide in the ribosomal RNA 28S, thus irreversibly blocking protein synthesis and causing cell death. Saporin can also be obtained recombinantly and not only from seeds.

The type of saporin is not especially limited but a preferred form of saporin is that known as SO-6. This form of saporin is unusual in that is highly stable to denaturants, proteases and heat. Moreover, in contrast to Type II RIPs (e.g. ricin), saporin lacks a cell-binding and internalization mechanism of its own and hence it is considered safe under normal conditions (Stirpe F, Gasper-Campani A, Barbieri L, Falasca A, Abbondanza A, Stevens W A (1983) *Ribosome-inactivating proteins from the seeds of Saponaria officinalis L. (soapwort) of Agrostemma githago L. (corncockle) and of Asparagus officinalis (asparagus) and from the latex of Hura crepitans L. (sandbox tree)*. Biochem J 216:617-625).

The conjugation of the first component and the second component is not especially limited but it has been found that a covalent conjugation is effective using a chemical linker such as bis-diazo-(-otolidine) [BDT]. Again the use of the linker and the compound used as the linker is not especially limited but those particular examples described above have been shown to work effectively.

A stoichiometric ratio of the first component to the second component in compounds in accordance with the present invention is not especially limited and may be in the range of 0.5:1 up to N:1 where N is the total number of binding sites for the first component in the second component. From those conjugates with stoichiometric ratios of the first component to the second component in the range of 0.5:1 to 14:1 without being especially limited conjugates in the range of 0.5:1 to 8:1 and preferably 0.5:1 to 2.5:1 may be effective in the treatment of ER+ cancer cells. The present inventors have surprisingly found that a ratio of approximately 2:1 of raloxifene:saporin results in the most effective conjugate for treatment of breast cancer cells whose use resulted in a significant initial reduction in the daily tumor volume as well as in an increased and sustained reduction in the rate of tumor growth. However, any conjugate for the present invention in the range of 0.5:1 to less than 8:1 may be equally effective.

A pharmaceutical composition comprising any compound of the present invention while not being especially limited may also comprise a pharmaceutically acceptable carrier, excipient and/or adjuvant.

The compounds and compositions in accordance with the present invention, while not being especially limited in use, are typically used for manufacture of a medicament for the treatment of cancers comprising ER+ cells, and are particularly useful in the treatment of breast, cancer, ovarian, cervical amongst other ER+ cancers.

The use of the compounds and compositions of the present invention is suitable for all mammals and particularly in humans.

The use may further be wherein the medicament is suitable for injection or infusion and without being especially limited particularly intravenously, subcutaneously or by any other means including oral administration.

The use is further suitable for injection into a subject to achieve a peak blood concentration of anywhere between 1% and 500% of the clinical peak blood concentration of the first component when used in an unconjugated form. In particular the use may be further suitable for injection to achieve 1% to 400% of the clinical peak blood concentration or further 1% to 300% or more particularly to achieve 1% to 200% and preferably between 80% and 140%. The inventors surprisingly found that treatment to achieve 80% and 140% with 2:1 raloxifene:saporin conjugate resulted in a significant initial reduction in the daily tumour volume compared to control results as well as an increased and sustained reduction in the rate of tumour growth without significantly impacting on non cancerous ER+ cells.

Unlike current cancer drugs, which act as antagonist competitors of estrogen (i.e they reduce the rate of cell division), the compound, pharmaceutical composition and treatment of the present invention has a lethal effect on cells bearing large numbers of ER receptors (i.e. cancer cells) but not on other ER+ cells. Cancer cell destruction caused by short term treatment reduces the scope for the phenotypic changes, typically observed in cancer cells under long-term exposure to antagonist competitors, leading to a loss of sensitivity for the competitor by the target cells. This product would suffer if the cancer cell mutated from ER+ to ER−. This product has two advantages over Herceptin (the humanised monoclonal antibody that acts on the HER2/neu receptors and is used in the treatment of breast cancer); firstly it targets ER+ cancer cells whether Her2/neu positive or not whereas Herceptin mainly targets Her2/neu positive cancer cells and secondly it destroys the cancer cells rather than just slowing the replication thereof. The product of the present invention does not have the shortcoming associated with photodynamic therapy as it can target cancer cells even if no light source can be focused on the cancer cells in question. This product is also superior to immunotoxins (i.e. monoclonal antibodies linked to a toxin) in that it should have a lower risk of vascular leak syndrome and nephrotoxicity due to immunocomplex formation.

In addition, independently of whether or not the SERM (carrier) and the type I RIP (toxin) are separated by the action of intracellular proteases on the linker after the conjugate has entered the target cell, the efficacy of the product would remain unaltered as it would be independent of the binding of the SERM to its receptor or any cellular mechanism activated by such binding. That is, once inside the cell, the type I RIP has a direct irreversible negative effect on ribosomes and hence on the translation of all mRNAs, either produced by housekeeping genes, induced as a result of stimulatory signals arising from the binding to and activation of any other cellular receptor (e.g. like that caused by the binding of the carrier SERM to a cellular receptor), or any other environmental or internal mechanism and/or stimulus.

DESCRIPTION OF THE FIGURES

The present invention will now be described in further detail by way of example only, with reference to the following discussion and to the accompanying drawings, in which.

EXAMPLES

Example 1

Conjugation of Raloxifene to Saporin

Raloxifene (Sigma) was conjugated to saporin (Sigma) using bis-diazo-(o-tolidine) [BDT] as a linker (this linker is useful for linking via tyrosine). The linker is fairly stable in acid solution, but reacts extremely rapidly with tyrosine and other aromatic phenols when the pH is raised to 7. For this reason the reaction is difficult to control. If not adequately controlled, the linker will cross-link saporin through the fourteen tyrosines in its sequence and destroy its integrity. Hence the conditions used are critical.

Conjugates were prepared at raloxifene to saporin ratios of 14:1, 8 (approx):1 and 2:1.

Below is provided a protocol for 2:1 (raloxifene:saporin) conjugation:

To carry out the conjugation a ten-fold molar excess of BDT per tyrosine (in saporin) was used and the reaction allowed to proceed between 30 seconds and over 50 seconds at −20° C. After raising the pH from 2 to 5 by adding the appropriate volume of molar sodium hydroxide solution in water (M.NaOHaq) the reaction was stopped by adding molar hydrochloric acid (M.HCl). UV spectroscopy analysis revealed that this resulted in, on average, two molecules of BDT reacting with each molecule of saporin for a reaction time of 30 seconds. Increased incubation times gave averages of eight and 14 molecules of BDT reacting with each molecule of saporin. The excess of BDT was used to favour the likelihood that each of these BDT molecules will have only reacted with one tyrosine. This means that the second diazo group in each of these two BDT molecules remained unreacted, and therefore available for reaction with raloxifene, which has three phenolic groups in its structure.

After gel filtration in M.HCl of the mixture to remove excess BDT, the BDT-saporin conjugates were reacted with a large excess of raloxifene in 50% methanol by raising the pH to 7. The solution was reacidified immediately, because raloxifene is stable in acid solution, but not in alkaline solution. Using a large excess of raloxifene ensured that it would be linked via BDT to saporin through only one of its phenolic groups, thereby being chemically modified only to the minimum extent possible and hence retaining its integrity as far as possible.

The reaction with raloxifene produced a brown solution and this colour was removed by extracting the solution with chloroform. The pale straw-coloured aqueous layer was evaporated to small volume at 40° C. under vacuum and centrifuged at 13000 RPM to remove solid matter. The pale yellow solution that was obtained was purified by gel filtration in M.HCl to give a colourless solution of the Raloxifene-BDT-saporin conjugate.

Example 2

Cell Lines

The MCF-7 cell line (ECACC, catalogue no. 86012803) was isolated from a breast adenocarcinoma in a 69 year old female and it expresses the estrogen receptor. The cell line was maintained in Minimum Essential Medium (Sigma) supplemented with 2 mM L-Gln (Sigma), 1% Non Essential amino acids (Sigma), 100 IU Penicillin, 100 µg/ml Streptomycin (Sigma) and, as complete medium, 10% Foetal Calf Serum (FCS) (Sigma).

The HCC-1143 cell line (ATTC, catalogue no. CRL-2321) was isolated from a breast primary ductal carcinoma in a 52 year old female and it does not express the estrogen receptor. The cell line was maintained in RPMI-1640 (Sigma) supplemented with 2 mM L-Gln (Sigma), 10 mM HEPES (Sigma), 1 mM Na-Pyr (Sigma), 100 IU Penicillin, 100 µg/ml Streptomycin (Sigma) and, as complete medium, 10% FCS (Sigma).

Finally, the NIH:OVCAR-3 cells (ATTC, catalogue no. HTB-161) was isolated from an ovary adenocarcinoma in a 60 year old female and it expresses the estrogen receptor. The cell line was maintained in RPMI-1640 (Sigma) supplemented with 2 mM L-Gln (Sigma), 10 mM HEPES (Sigma), 1 mM Na-Pyr (Sigma), 0.01 mg/ml Bovine Insulin (Sigma), 100 IU Penicillin, 100 µg/ml Streptomycin (Sigma) and, as complete medium, 20% FCS (Sigma).

Example 3

Clonogenic Assay

Cultures of MCF-7, HCC-1143 and OVCAR-3 were harvested at approximately 80% confluency by trypsinisation and after washing once in serum free medium, used to seed Flat bottom 96-well plates (Nunc) with $5\times10^3$ cells per well in 200 µl of complete medium.

After 48 hours incubation at 37° C., the medium was removed and substituted with 100 µl/well of several dilutions of the test (raloxifene:saporin conjugates in PBS) or control substances (saporin, raloxifene, PBS (Sigma) and finally Mitomycin C (Sigma) as a positive control) in complete medium in quadruplicate.

Following 18 hours incubation at 37° C., the test compounds were removed and 200 µl/well of complete medium added to each well.

After 96 hours incubation at 37° C. the medium was removed and 100 µl/well of 0.9% Triton X-100 (Sigma) in PBS at RT added to all wells. Following 2 hours incubation at 37° C., 50 µl of the PBS-Triton solution was transferred from all wells to a new flat bottom 96 well plate.

The detection reagent from the CytoTox 96® Non-Radioactive Cytotoxicity Assay kit (Promega) was prepared as per manufacturer's instruction and 50 µl/well of detection reagent was added to all wells. After 30 minutes incubation in the dark at room temperature, the reaction was stopped by adding 50 µl/well of Stop solution to all wells and the absorbance of each well at 490 nm was established.

Example 4

In Vivo Anti-Tumor Activity

Thirty (30) nude female mice (nu/nu), 6-8 weeks old, were challenged subcutaneously with $2\times10^7$ MCF-7 cells delivered in combination with Matrigel (Becton Dickinson) (200 µl total volume). Weight loss and tumor growth (calculated by taking two perpendicular measurements and applying the formula $[\Pi*((\min \text{ measurement})/2)^2*(\max \text{imum measurement})]$) were monitored daily until the end of the study.

When established tumours reached a volume of 0.3 cm³ (day 36 post challenge) animals were divided into groups of three (3) animals and each group was dosed intravenously (via the retro-orbital route) with either:

100 µl of Raloxifene:Saporin 2:1 conjugate (S:R 1:2) in PBS so as to obtain peak R:S 2:1 conjugate blood concentrations of 0.4, 0.2 and 0.1 nM, which are equivalent to 0.4, 0.2 and 0.1 ng/ml of Raloxifene respectively (i.e. three groups: A, B and C respectively)
 100 µl of Raloxifene in PBS again so as to obtain peak conjugate blood concentrations of 0.4, 0.2 and 0.1 ng/ml of raloxifene, (i.e. three groups: D, E and F respectively)
 100 µl of PBS, (i.e. one group: G)

The targeted blood concentrations of raloxifene are based in the human standard therapeutic peak concentration of raloxifene in blood (i.e. 0.5 ng/ml). Individual mouse doses to achieve this blood concentration of raloxifene, delivered either as a conjugate or as a pure product, were calculated by multiplying the individual weight of each mouse (g) by 0.08 (i.e. the blood volume of a mouse in ml is on average 8% of its weight) and by the desired blood concentration of Raloxifene (i.e. 0.4, 0.2 and 0.1 ng/ml).

Seven days after the first dose (day 43 post challenge), animals received a second dose of conjugate, pure Raloxifene or PBS in order to achieve the same final blood concentrations of Raloxifene (i.e. 0.4, 0.2 and 0.1 ng/ml).

Statistical Analysis

Statistical differences were calculated using non-parametric Mann-Whitney assays and considered significant if $p<0.05$.

Results

The study was aimed at establishing whether a conjugate of saporin and raloxifene can selectively kill estrogen receptor (ER) positive breast cells whilst not killing female genital tract ER-positive cells or other non-ER positive cells. For this purpose saporin was conjugated to raloxifene at molar ratios (R:S) of 14:1, 8:1 and 2:1 and test the effect of increasing doses of these conjugates on cell monolayers of MCF-7 (ER-positive breast cancer cell line), HCC-1143 (ER-negative breast cancer cell line) and OVCAR-3 (ER positive breast cancer cell line).

Figure 1:
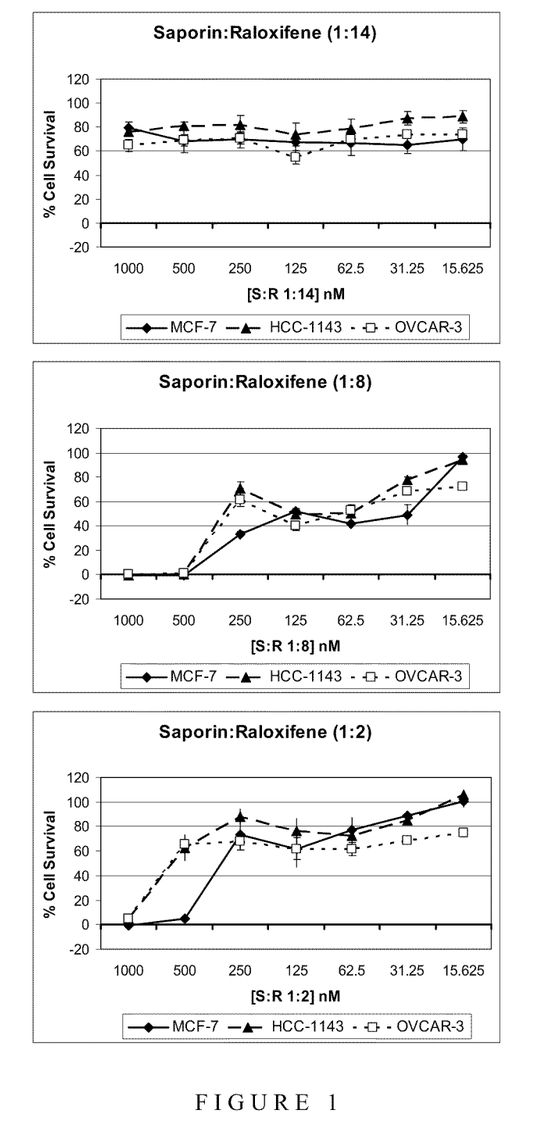
FIG. 1 shows the survival of MCF-7, HCC-1143 and OVCAR-3 cell monolayers exposed to decreasing concentrations of different saporin:raloxifene (S:R) conjugates. Cell survival (%) for each cell line is calculated according to a standard lactate dehydrogenase (LDH) release assay, where minimum release (0% survival) corresponds to cells treated with 50 μg/ml of Mitomycin C and maximum release (100%) survival corresponds to cells treated only with complete medium.

As shown in FIG. 1, raloxifene:saporin 14:1 conjugate (S:R 1:14) had limited effect on any of the cell lines and certainly no selective lethal effect against MCF-7 cells compared to either HCC-1143 or OVCAR-3. In contrast, raloxifene:saporin 8:1 conjugate (S:R 1:8) proved to be lethal to all cell lines at conjugate concentrations at or above 500 nM. Only at a 250 nM concentration can a small increase in the selective lethal effect against MCF-7 cells be observed (33.6±2% MCF-7 survival vs 70.8±5% HCC-1143 and 61.2±5.6% OVCAR-3 survival).

Similarly to raloxifene:saporin conjugate 8:1 (S:R 1:8), the raloxifene:saporin conjugate 2:1 (S:R 1:2) killed all cells irrespective of ER status at the highest conjugate concentration tested. However, at lower doses, raloxifene:saporin 2:1 conjugate had the most significant selective effect of all three conjugates tested. At a conjugate concentration of 500 nM, raloxifene:saporin 2:1 conjugate killed most MCF-7 cells (4.9±4.3% survival) whilst having only a limited effect on HCC-1143 (62.8±10.7% survival) and OVCAR-3 (65.2±3.5% survival).

In view of these results raloxifene:saporin conjugate 2:1 was selected for further detailed in vitro analysis. For this purpose MCF-7, HCC-1143 and OVCAR-3 cell monolayers were treated with raloxifene:saporin 2:1 at 500 nM as well as with the molar concentration equivalents of Saporin (500 nM), Raloxifene (1000 nM) and an admixture (i.e. unconjugated) of Saporin (500 nM) and Raloxifene (1000 nM).

Figure 2:
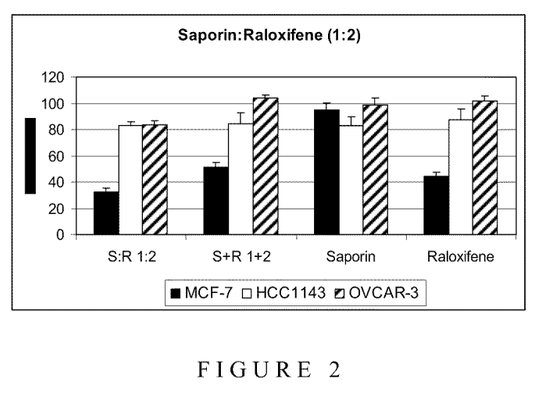
FIG. 2 shows the survival of MCF-7, HCC-1143 and OVCAR-3 cell monolayers exposed to either 500 nM raloxifene:saporin 2:1 conjugate (S:R 1:2 conjugate) or the molar concentration equivalents of saporin (500 nM), raloxifene (1000 nM) and of an admixture (i.e. unconjugated) of saporin (500 nM) and raloxifene (1000 nM). Cell survival (%) for each cell line is calculated according to a standard lactate dehydrogenase (LDH) release assay, where minimum release (0% survival) corresponds to cells treated with 50 μg/ml of Mitomycin C and maximum release (100%) survival corresponds to cells treated only with complete medium.

As shown in FIG. 2, which represents the average of two independent experiments Raloxifene had a selective significant (p<0.05) effect against the ER positive breast cancer MCF-7 cell line, but not against the ER-negative HCC-1143 cell line or the ovarian ER positive OVCAR-3 cell line. Similarly, the Saporin and raloxifene admixture had a selective effect on the MCF-7 cells that can be most likely traced to the activity of raloxifene since no significant (p>0.05) lethal effect could be attributed to saporin on its own. Conjugation of raloxifene to saporin at a 2:1 molar ratio, compared to a simple admixture of both compounds, caused a significant increase (p, 0.05) in the lethal effect of the compounds against MCF-7 (16.0±6.3% vs 51.6±3.2% in MCF-7 survival) but had only a limited increment on the lethal effect against HCC-1143 (72.4±5.7% vs 84.3±8.5% in HCC-1143 survival) and OVCAR-3 cells (77.7±4.9% vs 104.4±2.5% in OVCAR-3 survival).

To test the efficacy of the raloxifene:saporin 2:1 conjugate (S:R 1:2) to control tumor growth in vivo, female nude mice (nu/nu) were challenged subcutaneously with MCF-7 cells. Once the tumors were established (day 36), the mice were treated with intravenous bolus injections of raloxifene:saporin 2:1 (S:R 1:2) via the retro-orbital route in order to achieve raloxifene:saporin 2:1 (S:R 1:2) peak blood concentrations of 0.4, 0.2 and 0.1 nM. These concentrations are the equivalent of those necessary to achieve raloxifene peak blood concentrations of 0.4, 0.2 and 0.1 ng/ml, which constitute 80%, 40% and 20% respectively of the target peak clinical blood concentration of raloxifene in humans. Control animals received either PBS or the same doses of raloxine via the same route. On day 43 animals received a second dose of either raloxifene:saporin 2:1 (S:R 1:2), PBS or raloxifene.

Figure 3:
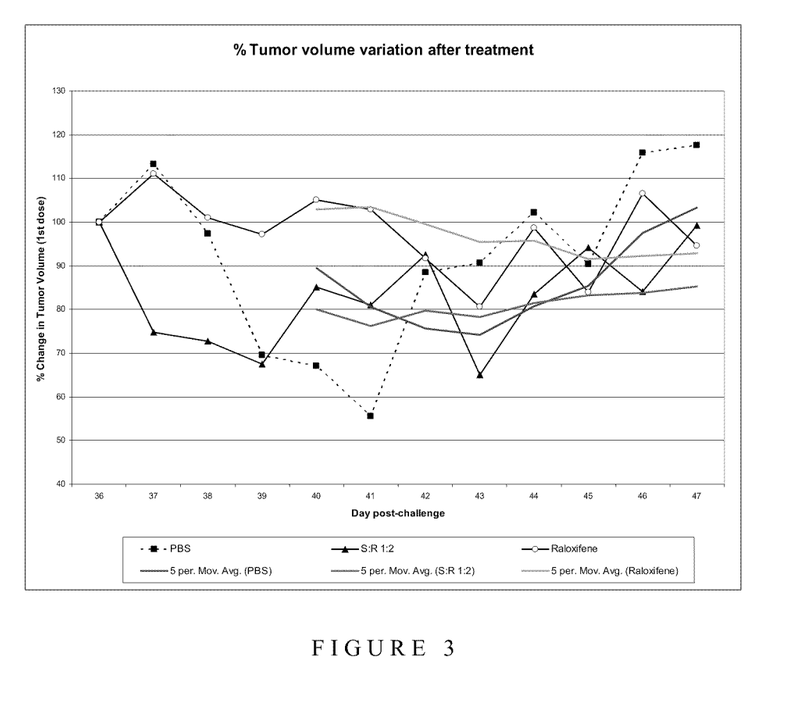
FIG. 3 shows the growth profile of MCF-7 tumors established in nude female mice following treatment with either Phosphate buffered saline (PBS), 0.4 ng/ml raloxifene or 0.4 nM of raloxifene:saporin 2:1 conjugate (S:R 1:2). Animals received intravenous treatment via the retro-orbital route on days 36 and 43 post challenge.

Due to the natural susceptibility of MCF-7 cells to estrogen production, daily tumor volume variation in the nude mice model used follows sinusoidal pattern with a period of approximately 4/5 days (see FIG. 3). The duration of this period correlates with the duration of the oestrus cycle in mice (i.e. 4/5 days). As a result, and in order to facilitate experimental analysis, FIG. 3 represents tumor volume variations for each experimental group both as daily changes and as moving averages (i.e. a trend line) for overlapping 5 day periods (i.e. overlap is 4 days per point).

The PBS treated group followed the sinusoidal pattern of tumor growth described above. This pattern is characterised by a natural trend to increase the maximum tumor volume attained in each cycle leading finally to a lethal tumor size. Treatment with 0.2 and 0.1 ng/ml of raloxifene did not result in any changes compared to the PBS control group. Only the 0.4 ng/ml Raloxifene group showed a natural trend for the maintenance or slight reduction of tumor size over time, which is characteristic of its mode of action in the clinic as a selective estrogen receptor modulator.

Treatment with 0.2 and 0.1 nM peak blood concentrations of raloxifene:saporin 2:1 (S:R 1:2) also failed to induce any changes in tumor growth compared to the PBS control group. However, treatment with 0.4 nM raloxifene:saporin 2:1 (S:R 1:2) resulted in a significant initial reduction in the daily tumor volume compared to the 0.4 ng/ml raloxifene and PBS groups (see FIG. 3, daily tumor volume change for days 37 and 38) as well as in an increased and sustained reduction in the rate of tumor growth compared to that achieved in the 0.4 ng/ml raloxifene group (see FIG. 3, moving average trend line for the study).

Example 5

In Vitro Activity of the Conjugate

The objective of this study was to evaluate the effects of the conjugate on the growth dynamics of subcutaneous ZR-75-1, an estrogen receptor positive human breast carcinoma cell line, implants in nude mice.

For this study and as ZR-75-1 growth is dependent on estrogen, no less than 40 normal female athymic nude mice (nu/nu) of 4-6 weeks of age were injected daily with 5 mg/kg estradiol starting at 3 days before tumor cell challenge. After the estradiol treatment, all animals were inoculated subcutaneously with $25 \times 10^6$ ZR-75-1 cells (obtained from the ATCC) in Matrigel (Becton-Dickinson) using a 21G needle and syringe.

Body weights and tumor volumes were monitored every 48 to 72 hours for 36 days after the first administration of the test substances. Tumor volumes were established using the formula: Tumor Volume=$(a^2 \times b/2)$, where 'a' is the smallest diameter and 'b' is the largest diameter.

Once the established tumors reached approximately 75-150 mm$^3$ (individual tumor volumes may range from 100 to 250 mg) the mice were assigned into three treatment groups (n=12 for each group) such that the mean tumor volumes among the seven groups are within 10% of the mean tumor weight of the control group. On the same day (Day 1), animals were injected intravenously with 0.1 ml of either (a) the Saporin-Raloxifene conjugate, (b) a mixture of unconjugated Saporin and Raloxifene, or (c) Raloxifene only. This treatment was repeated every 72 hours for a total of five times (Days 1, 3, 6, 9 and 12).

The net amount of Raloxifene injected per animal in all three groups was the same and it was designed to give a peak Raloxifene concentration in blood of 0.7 ng/ml, which is within the range of Raloxifene concentration in blood in the clinic. Those animals also injected with Saporin, either free or conjugated to the Raloxifene, received the same amount of Saporin calculated on a Saporin:Raloxifene molar ratio of 1:2.

Estradiol dosing was resumed 15 days after implantation to foster normal growth of the subcutaneous tumors.

The mice were euthanized (via $CO_2$ asphyxiation) if the animal was found moribund or if the body weight decreased below 14 g. Euthanasia was also performed if the individual tumor volume reached 3,000 mm$^3$ or if the tumor became ulcerated. During the study one animal from Group B (unconjugated Saporin and Raloxifene) had to be removed from the study.

The results of this study suggest that administration of the Saporin-Raloxifene conjugate in a significant (p<0.05, Mann-Whitney) reduction of the peak tumor volume achieved (Day 5) compared to administration of either Raloxifene alone or Raloxifene and Saporin unconjugated.

Figure 4:
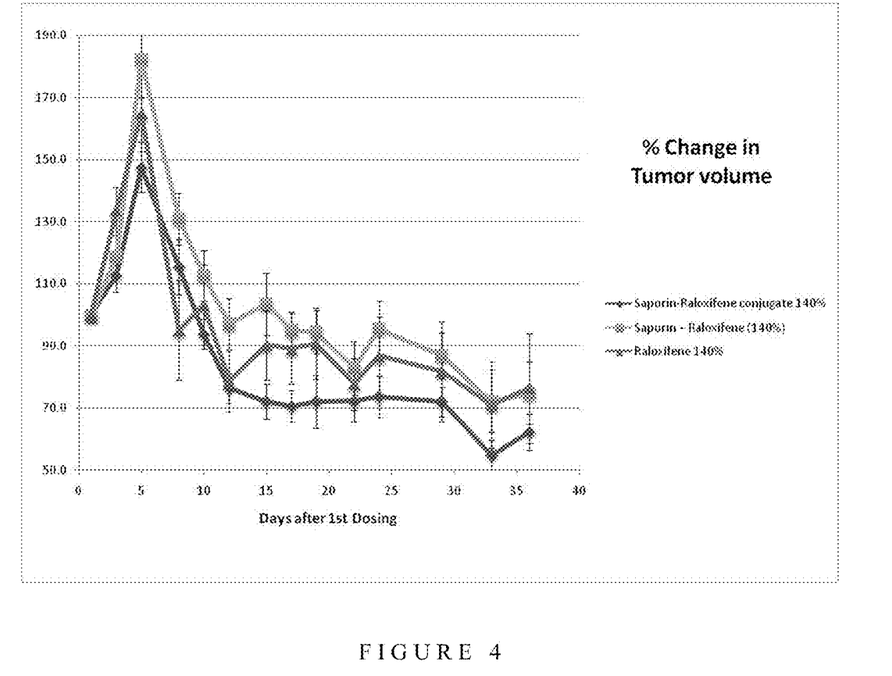
FIG. 4 shows the percentage change in tumor volume for treatment with the conjugate as compared with control and unconjugated product.

Moreover, at the end of the treatment (Day 12) and up to Day 36, animals dosed with the Saporin-Raloxifene conjugate generally showed consistently reduced tumor volumes compared to the other two experimental groups (see FIG. 4).

Figure 5:
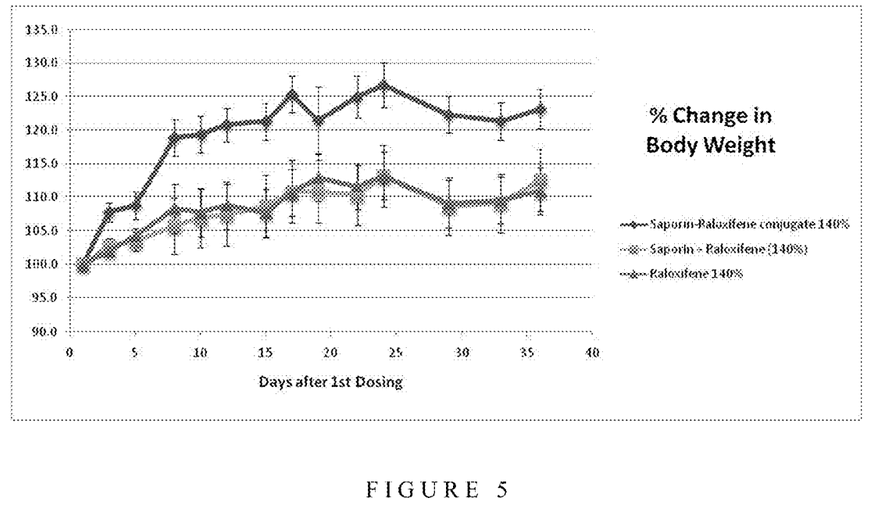
FIG. 5 shows the percentage change in body weight for treatment with the conjugate as compared with control and unconjugated product.

An indication of the general health of an animal can be obtained through the observation of the animals' body weight over the course of a study. Therefore, mice from each group were weighed every 48 to 72 hours throughout the entire study. The results clearly show that animals dosed with the Saporin-Raloxifene conjugate had a significantly (p<0.05, Mann-Whitney) better weight gain profile that those dose with either Raloxifene alone or Raloxifene and Saporin unconjugated (see FIG. 5).

Example 6

Further Conjugation of Raloxifene to Saporin

Experiment A

Raloxifene (Sigma) was conjugated to saporin (Sigma) using bis-diazo-(o-tolidine) [BDT] as a linker. This linker is fairly stable in acid solution, but reacts extremely rapidly with tyrosine and other aromatic phenols when the pH is raised to 7. For this reason the reaction is difficult to control. If not adequately controlled, the linker will cross-link saporin through the fourteen tyrosines in its sequence and destroy its integrity. Hence the conditions used are important.

Conjugates were prepared at raloxifene to saporin ratio of 2:1.

A protocol for 2:1 (raloxifene:saporin) conjugation is provided below: slightly sonicated To carry out the conjugation 1.2 mg of lyophilised Saporin (Sigma) was dissolved in 0.6 ml of water. To this solution, 0.4 ml of DMSO (Sigma) and 0.01 ml of 1M HCl were added DMSO and mixed. After slight sonication of the resulting protein solution, between 0.4 and 1 mg of Raloxifene were added to the solution followed by a molar excess of BDT per tyrosine (in saporin). The pH of the resulting solution was raised to 6.5 by adding the appropriate volume of molar sodium hydroxide solution in water (M.NaOHaq) and the reaction was allowed to proceed between 22 and 34 minutes at room temperature. At the end of the reaction, phosphoric acid was added to the solution to a final concentration of approximately 9 and mixed. Excess BDT was removed from the crude conjugate solution by elution through a Biogel P2 Column (BioRad) using a solution of 30.4% DMSO and 9.1% Phosphoric acid in water as eluent. Fractions containing Saporin and Raloxifene were determined by UV spectrophotometry and dialysed against water before use.

Experiment B

Raloxifene-HCl and DSC (Di-(N-succinimidyl)carbonate—this linker is useful in binding via lysine) were dissolved at a mass ratio of 2:1 (Raloxifene:DSC) in 0.2 ml DMF (dimethylformamide). Triethylamine (0.01 ml) was added to pyridine (0.13 ml) and aliquots (0.01 ml) of this preparation were added sequentially to the Raloxifene/DSC mixture over a period of 15 minutes. This process was carried out at 21° C. and under constant agitation. A solution of Saporin (0.6 mg/ml) was prepared in mixture of 40% DMF in 15 mM Sodium Phosphate buffer pH 7.4 and 0.01 ml of the Raloxifene/DSC solution added. The resulting preparation was first mixed by vortexing and then sonicated until it attained a colloidal appearance before allowing the conjugation reaction to proceed for 30 minutes at 21° C. The resulting products was centrifuged at 13000 rpm for 3 min and the clarified supernatant was either used directly or passed through a Sephadex G10 column in 0.1 HCl, freeze dried and re-suspended in PBS before use.

Experiment C

Saporin was dissolved in 10 mM phosphate buffer pH 6.0 containing 2 mg/ml glucose and to the resulting solution, 0.1 ml of molar HCl was added under constant agitation so as to reduce the pH to 3.7. To this preparation, 1 ml of a solution of Raloxifene-HCl in DMSO (3 mg/ml) was added under constant agitation at 21° C. followed by 0.005 ml of the BDT reagent. Small aliquots (0.01 ml) of 0.1 M NaOh were sequentially added to the continually stirred Saporin-Raloxifene-BDT preparation in order to bring the pH to 6.8 at which point the reaction was allowed to continue for 60 minutes. The resulting product was dialysed overnight first against water and afterwards against PBS containing 2 mg/ml glucose. The brown precipitate that developed during the process was collected and re-dissolved in water by ultrasonication and extensive vortexing. After clarification by centrifugation, the supernatant was aliquoted ready for use.

The invention claimed is:

1. A compound comprising:
    (a) a first component capable of binding to estrogen receptor positive (ER+) cell receptors, wherein the first component is a selective estrogen receptor modulator (SERM); and
    (b) a second component; wherein the second component is a ribosome inactivating toxin;
    wherein the first component is covalently conjugated to the second component using a chemical linker; and
    wherein the stoichiometric ratio of the first component conjugated to the second component is in the range of from 2:1 to 8:1.

2. The compound of claim 1, wherein the ribosome inactivating toxin is saporin, momordin (MOM), pokeweed antiviral protein from seeds (PAP-S), bouganin or gelonin.

3. The compound of claim 2, wherein the ribosome inactivating toxin is saporin.

4. The compound of claim 1, wherein the first component is a raloxifene compound.

5. The compound of claim 1, wherein the chemical linker is bis-diazo-(o-tolidine).

6. The compound of claim 1, wherein a stoichiometric ratio of the first component to the second component is in the range of from 2:1 to 5:1.

7. The compound of claim 6, wherein the stoichiometric ratio of the first component to the second component is in the range of from 2:1 to 2.5:1.

8. A pharmaceutical composition comprising a compound of claim 1 and a pharmaceutically acceptable carrier, excipient and/or adjuvant.

9. A method of treating a cancer comprising ER+ cancer cells comprising contacting a subject in need of such treatment with the compound of claim 1 or composition of claim 8.

10. The method according to claim 9, wherein the cancer is breast cancer, ovarian cancer, cervical cancer, or other ER+ cancers.

11. The method according to claim 9, wherein the subject is a mammal.

12. The method according to claim 11, wherein the mammal is a human.

13. The method according to claim 9, wherein the compound or composition is suitable for injection or infusion in a subject or is suitable for oral administration in a subject.

14. The method according to claim 13, wherein the compound or composition is in an amount suitable to achieve peak blood concentrations of the conjugate equivalent to 1% to 500% of the clinical peak blood concentration of the first component when used in an unconjugated form.

15. The method according to claim 14, wherein the compound or composition is in an amount suitable to achieve peak blood concentrations of the conjugate equivalent to 80% to 140% of the clinical peak blood concentration of the first component when used in an unconjugated form.

16. A method of manufacturing a compound of claim 1, wherein the method comprises reacting the first and second components to conjugate the first component to the second component.

17. The compound of claim 1, wherein the ribosome inactivating toxin is a type I ribosome-inactivating protein.

18. The compound of claim 1, wherein the first component is a droloxifene compound, a fulvestrant compound, a idoxifene compound, a lasofoxifene compound, a raloxifene compound, a tamoxifen compound, or a toremifene compound.

\* \* \* \* \*